(12) United States Patent
Eisele

(10) Patent No.: US 9,716,140 B2
(45) Date of Patent: Jul. 25, 2017

(54) FLUID SENSOR AND METHOD FOR EXAMINING A FLUID

(71) Applicant: Fraunhofer Gesellschaft zur Foerderung der angewandten Forschung e. V., Munich (DE)

(72) Inventor: Ignaz Eisele, Icking (DE)

(73) Assignee: Fraunhofer Gesellschaft zur Foerderung der angewandten Forschung e. V., Munich (DE)

( * ) Notice: Subject to any disclaimer, the term of this patent is extended or adjusted under 35 U.S.C. 154(b) by 0 days.

(21) Appl. No.: 14/674,850

(22) Filed: Mar. 31, 2015

(65) Prior Publication Data

US 2015/0287781 A1 Oct. 8, 2015

(30) Foreign Application Priority Data

Apr. 2, 2014 (DE) .................. 10 2014 104 661
Mar. 24, 2015 (DE) .................. 10 2015 104 419

(51) Int. Cl.
| | | |
|---|---|---|
| G01N 27/414 | (2006.01) | |
| H01L 29/78 | (2006.01) | |
| H01L 29/06 | (2006.01) | |
| H01L 27/06 | (2006.01) | |

(52) U.S. Cl.
CPC ....... *H01L 29/0657* (2013.01); *G01N 27/414* (2013.01); *H01L 27/0629* (2013.01); *H01L 29/78* (2013.01); *Y10T 436/205831* (2015.01); *Y10T 436/214* (2015.01); *Y10T 436/22* (2015.01)

(58) Field of Classification Search
CPC . H01L 29/0657; H01L 29/78; H01L 27/0629; G01N 27/414; Y10T 436/214; Y10T 436/205831; Y10T 436/22
See application file for complete search history.

(56) References Cited

U.S. PATENT DOCUMENTS

| | | | |
|---|---|---|---|
| 4,877,582 A | 10/1989 | Oda et al. | |
| 2006/0154399 A1 | 7/2006 | Sauer et al. | |
| 2007/0295988 A1* | 12/2007 | Yamamoto | G01N 27/4145 257/147 |
| 2011/0068015 A1* | 3/2011 | Park | G01N 27/4145 205/792 |
| 2011/0108892 A1* | 5/2011 | Monfray | G01N 33/54373 257/253 |

(Continued)

FOREIGN PATENT DOCUMENTS

| | | |
|---|---|---|
| DE | 3727805 A1 | 3/1988 |
| DE | 19814857 A1 | 10/1999 |
| DE | 10211900 A1 | 10/2003 |

(Continued)

OTHER PUBLICATIONS

Korotcenkov, Ghenadii , "Chemical Sensors", Comprehensive sensors technologies, vol. 4: solid-state devices, p. 187-227.

*Primary Examiner* — Paul Hyun
(74) *Attorney, Agent, or Firm* — Murphy, Bilak & Homiller, PLLC

(57) ABSTRACT

Embodiments relate to a fluid sensor and a method for examining a fluid. A fluid sensor includes a substrate which comprises a recess for receiving a fluid to be examined, wherein the fluid sensor is implemented to detect electrical changes in the recess caused by the fluid to be examined.

15 Claims, 8 Drawing Sheets

(56) References Cited

U.S. PATENT DOCUMENTS

2013/0056367 A1 3/2013 Martinez et al.

FOREIGN PATENT DOCUMENTS

| DE | 102013001035 A1 | 1/2014 |
| EP | 1103808 A2 | 5/2001 |
| GB | 2498522 A | 7/2013 |
| WO | 0075649 A1 | 12/2000 |
| WO | 2012170630 A2 | 12/2012 |

* cited by examiner

FLUID SENSOR AND METHOD FOR EXAMINING A FLUID

PRIORITY CLAIM

This application claims priority to German Patent Application No. 10 2014 104 661.7 filed on Apr. 2, 2014 and to German Patent Application No. 10 2015 104 419.6 filed on Mar. 24, 2015, the content of both of said applications incorporated herein by reference in their entirety.

TECHNICAL FIELD

Embodiments relate to a fluid sensor and a method for examining a fluid.

BACKGROUND

From conventional technology, potential changes on the surface of a solid body due to chemical reactions are known. For example, these potential changes may be measured using a so-called "Kelvin probe", wherein a plate capacitor having a mechanically moved electrode is used. Due to the mechanical movement a charge transfer results which is detected via voltage (difference of the surface potentials of the two electrodes or "contact potential difference" (CPD)). If a chemical reaction changes the charge on an electrode surface, the resulting change of the CPD, i.e. the change of the electric field, may be measured. To acquire reliable measurements it is desirable for one of the two electrodes not to be chemically reactive, i.e. to be inert, e.g. in the sense of a reference electrode. Otherwise, a reaction of the chemically sensitive electrode might not be determined correctly.

On the basis of the Kelvin probe there have been numerous developments. In order to avoid using the mechanically moved electrode, field effect transistors (FETs) have been used, wherein a potential change leads to a transfer or shift of the initial voltage and thus to a current change. FETs having a metal insulator semiconductor structure turned out to be especially suitable, see also (MISFETs). The metal insulator semiconductor structure may here form a capacity between a metal layer and a semiconductor layer. By the MIS capacitor, with the help of a voltage at the metal (also "gate") a charge may be influenced in the semiconductor. The same controls the current between two electrodes (also "source/drain").

For the application of MISFETs as gas or liquid sensors, an air gap between the metal and the insulator is realized and a chemically sensitive layer is applied on the side of the metal facing the insulator. Embodiments are of the suspended gate FET (SGFET), the hybrid SGFET (HSGFET) and the charge coupled FET (CCFET). The MIS capacity may be reduced by the additional air gap, and consequently also the current control factor for the transistor and thus also the sensitivity regarding chemically-generated potential changes. An improvement may be reached by using an insulated gate, also known as "floating gate" (FGFET). Here a center tap is introduced into an MIS capacitor having an air gap, which is connected to a conventional metal oxide layer FET (MOSFET) as a "floating"/insulated electrode.

Although the chemically generated potential changes at the center tap decreases due to the capacitive voltage division, all in all an improvement of the sensitivity may result as the amplification factor of the MOSFET may be fully utilized. With this concept, the gate electrode of the MIS capacitor is provided with a chemically sensitive layer which may be problematic. The opposing electrode is covered by an insulator. The air gap is located between this insulator and the gate electrode. The open insulator surface may be problematic as it may also react chemically, e.g. due to moisture, corrosion, etc.

Apart from that, a free surface has a finite resistance which may lead to drift phenomena due to the electrical fields within the capacitor.

For being applied as a liquid sensor, the metal electrode (the gate of the MISFET) is replaced by a conductive liquid (ISFET). If the liquid is provided with a reference electrode, at the insulator/liquid interface a space charge region forms within the liquid whose width depends on the ion concentration. The thus resulting capacity change changes the current control factor of the transistor and thus enables the measurement of the ion concentration in the liquid. Also here, a stable reference electrode in the liquid is of importance.

SUMMARY

It is thus desirable to provide an improved concept for a fluid sensor.

Some embodiments are based on the idea that a recess in a substrate may be used to examine a fluid, e.g. a gas, a liquid or a plasma. Embodiments provide a fluid sensor, chemical sensor or chemosensor with a substrate comprising a recess for receiving a fluid to be examined. The fluid sensor is implemented to detect electrical changes in the recess caused by the fluid to be examined. Embodiments thus simplify the setup of a fluid sensor. The use of a recess in the substrate may enable a simple manufacturing and advantageous arrangement of the electrodes.

It is a further central idea of embodiments to at least partially reduce, to control or to shield an electric field in the recess caused by exterior influences. In some embodiments, the fluid sensor further includes an exterior electrode which at least partially surrounds the recess and is connected or connectable to a reference potential. In so far, embodiments may reduce the influence of exterior electrical fields onto a measurement using the fluid sensor. In further embodiments, the exterior electrode may correspond to a demarcated doping area of the substrate. In other words, a substrate may be used which for example corresponds to a semiconductor substrate and which includes one or several doping areas having different dopings. The exterior electrode may then be realized with little effort in the substrate via a doping. In some embodiments, the exterior electrode may in so far also be implemented protectedly, i.e. such that no direct contact between the exterior electrode and the fluid to be examined results and the exterior electrode is inert.

Apart from that, in some embodiments the exterior electrode may be used to set an operating point of the fluid sensor or a transistor of the fluid sensor via the reference potential, in particular in order to switch on and off the fluid sensor, for example to guarantee an energy efficient operation of the sensor outside measurement phases, or to set the same into a sleeping mode, respectively, in which an energy consumption as compared to a measurement mode is reduced. For example, in an idle mode an idle mode potential may be applied to the exterior electrode, so that independent of a fluid in the recess a transistor for detecting the electrical change is kept in a non-conductive state. By applying an operating point potential which is selected so that a transistor for detecting the electrical change operates at a certain operating point of its characteristic curve (e.g. linear range or saturation range), for example, a sensitivity of the fluid sensor may be influenced. Alternatively, the operating point potential may also be varied during the detection of the electrical change (e.g. for examining liquids). In some embodiments the fluid sensor may also be completely switched off via the reference potential, i.e. basically be set into a currentless or powerless mode.

Some embodiments may avoid an open reference electrode and still acquire a shielding, like e.g. by a Faraday cage. The shielding or exterior electrode here comprises openings for the entry of gases and/or liquids. For example, in case of a plate capacitor two electrodes are used and the electric field in the interior is constant. With a Faraday cage, a basically self-contained (apart from the mentioned openings) electrode may be used and a potential in the interior may virtually be kept constant. By this, a "chemically inert" second electrode may be implemented more easily or be avoided, respectively, or critical effects accompanied by an open electrode may be avoided.

Some embodiments thus include a Faraday cage or an electrode which is basically self-contained and thus virtually forms a Faraday cage, the Faraday cage being provided with one or several openings which enable gas or a liquid to enter or exit. This may e.g. be a conductive hollow cylinder, a conductive trench structure, a conductive ball having openings, etc. If a potential is applied to the conductive structures from the outside, apart from boundary effects at the openings, the potential in the interior of the structure may basically be kept constant, in some embodiments even substantially field-free. For the boundary effects to become negligible, in one embodiment for example of a hollow cylinder the length (extent in the direction perpendicular to the basically circular base area) may be much longer than a diameter of the base area. In one embodiment of a trench, a trench depth may be a lot larger, i.e. twice as large as a trench width.

It is a further basic idea that in the interior of a Faraday cage a chemically sensitive layer may be applied wherein due to gases or liquids for example the formation of charges and/or dipole moments may result and thus a potential in the interior may be changed. The value of the potential change may e.g. be measured by an insulated or "floating" electrode which like in case of the "floating gate" FET (FGFET) is connected to the gate of an MOSFET, as will be explained in more detail in the following. Apart from that, embodiments may be based on the finding that instead of potential difference measurements or relative potential measurements (like for example by means of capacities), also absolute potential measurements may be executed and that with these potential measurements a counter electrode in the conventional sense may be omitted. Deviations which may be due to a non-inert second electrode may thus be reduced or excluded. Embodiments may thus enable a more reliable or temporally more stable detection of the electrical changes. Embodiments thus provide a fluid sensor which is implemented to detect an absolute potential change at an electrode, like e.g. at a gate of an FET, caused by a fluid to be examined. The fluid sensor may comprise an electrode configured to develop an absolute potential change caused by a fluid to be examined.

Embodiments further provide a method for examining a fluid. The method includes passing the fluid through a recess of a substrate and detecting an electrical change in the recess.

In some embodiments, the fluid sensor may include a transistor which is implemented to detect the electrical changes in the recess as potential changes. In so far, the transistor may be integrated in the sensor, for example the transistor may be formed on the same substrate as the sensor or integrally with the sensor in order to thus enable a compact sensor and a simple manufacturing method. In some embodiments, the transistor may be formed as an insulated gate field effect transistor. The insulated gate may at least partially be arranged within the recess. Some embodiments may thus provide an efficient fluid sensor with a sufficient sensitivity, wherein the transistor may also be arranged outside the recess. In some embodiments, the fluid sensor may comprise a chemically sensitive layer which is at least partially arranged in the recess. In so far, electrical changes which are for example caused by chemical reactions, the passage of ions, physical adsorption, chemical adsorption, etc. may be detected and measured or be further processed. As already mentioned above, an operating point of such a transistor which may occur in a self-conducting (normally conducting) or also in a self-locking (normally locking) form in embodiments may be determined so that different operating modes of the fluid sensor are enabled.

It is a further basic idea that with a fluid sensor an insulated gate of a field effect transistor is at least partially shielded by an electrode so that electrical changes, e.g. a potential change, due to a fluid to be examined, may be detected by the gate and thus the transistor. Embodiments provide a fluid sensor having a transistor which is implemented to detect an electrical change caused by a fluid to be examined, e.g. of a chemically sensitive layer. The transistor is implemented as an insulated gate field effect transistor and the insulated gate and a recess for receiving the fluid to be examined are at least partially surrounded by a common shielding electrode. Some embodiments may thus reduce the influence of interferences and/or increase a sensitivity of a fluid sensor. The recess may here be outside a substrate on which the transistor is formed and may at least be partially surrounded by the insulated gate.

In further embodiments, in the recess a boundary layer towards the fluid to be examined is formed by the chemically sensitive layer. In other words, the chemically sensitive layer may be directly exposed to the fluid to be examined, for example when the fluid passes the recess in the substrate, and may thus make electrical changes measurable. In some embodiments, the chemically sensitive layer may at least partially and at least with respect to two spatial directions surround the fluid to be examined in the recess. In so far, the chemically sensitive layer and/or the exterior electrode may form a passage, channel or trench for the fluid to be examined. In so far, embodiments may provide an arrangement in different layers which may be manufactured with little cost and effort by corresponding processes, e.g. thin-film coating processes.

Some embodiments include the above-described insulated gate and the above-described exterior electrode. The insulated gate may at least partially be arranged between the chemically sensitive layer and an exterior electrode, so that an electric field at the insulated gate may be influenced by the chemically sensitive layer and the gate is at least partially shielded by the exterior electrode. In further embodiments, the fluid sensor at least partially includes an insulation layer which is at least partially arranged between the substrate and the chemically sensitive layer. The insulated gate may at least partially be separated from the chemically sensitive layer and the exterior electrode by one or several insulation layers. In so far, embodiments may comprise several layers, for example a substrate, an exterior electrode, an insulation layer, a gate, a further insulation layer, a chemically sensitive layer.

Some embodiments of the fluid sensor may include a gate oxide layer for the transistor which is implemented to be thinner than the one or several insulation layers. Some embodiments may thus realize an improved sensitivity.

The recess may comprise a vertical extent which is at least twice as large as a lateral extent of the recess along other spatial directions. In so far, the recess may have a longitudinal form, for example in the form of a bore, a tunnel, etc. In some embodiments, accordingly the extent of the recess along a path which the fluid to be examined takes in the recess may be larger than an extent of the recess in directions orthogonal to this path. The recess may for example be implemented in the form of a trench, in the form of a passage or in the form of a gap. In some embodiments, the recess may be implemented as a passage through the substrate from a first side of the substrate to a second side of the substrate, for example as a breakthrough, passage, bore, via.

It is a further central idea to provide a passage in a substrate of a fluid sensor in which by means of a chemically sensitive layer an electrical change may be detected. Embodiments thus provide a fluid sensor which comprises a chemically sensitive layer in a passage of a substrate for receiving a fluid to be examined. The sensor further includes a transistor which is implemented to detect an electrical change of the chemically sensitive layer in the passage caused by the fluid to be detected. Embodiments may thus provide a fluid sensor for a fluid involving little cost or effort. In some embodiments, the passage may basically be implemented in the shape of a hollow cylinder. The transistor may be implemented as an insulated gate field effect transistor. The insulated gate may at least partially extend along a wall of the hollow cylinder-shaped recess of the substrate. The fluid sensor may further include an exterior electrode which at least partially surrounds the recess or shields the same, respectively, or at least reduces exterior field influences on a field within the recess. The substrate may for example at least be a part of a semiconductor wafer.

BRIEF DESCRIPTION OF THE DRAWINGS

In the following, embodiments are explained in more detail with reference to the accompanying drawings, in which.

DESCRIPTION

Figure 1A:
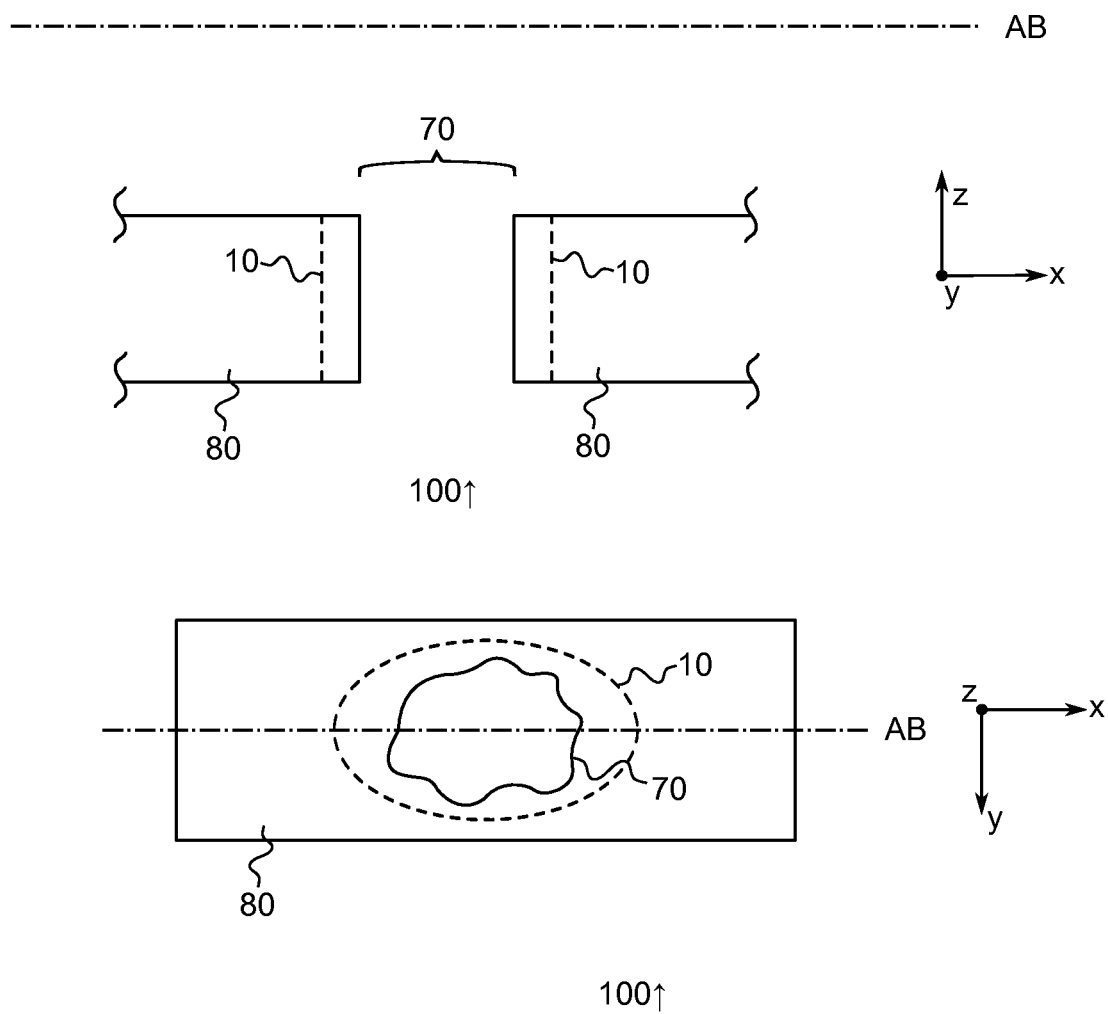
FIG. 1a shows one embodiment of a fluid sensor from two perspectives with an optional exterior electrode.

Different embodiments are now described in more detail with reference to the accompanying drawings in which some embodiments are illustrated. In the Figures, the thicknesses of lines, layers and/or regions may be exaggerated for clarity.

In the following description of the accompanying drawings which merely show some exemplary embodiments, like reference numerals may designate like or comparable components. Further, summarizing reference numerals may be used for components and objects which occur several times in an embodiment or in a drawing but which are commonly described with respect to one or several features. Components or objects designated by the same or summarizing reference numerals may be implemented alike but also differently with respect to individual, several or all features, like e.g. the dimensioning, as far as the context does not implicitly or explicitly indicate otherwise.

Accordingly, while example embodiments are capable of various modifications or alternative forms, embodiments thereof are shown by way of example in the Figures and will herein be described in detail. It should be understood, however, that there is no intent to limit example embodiments to the particular forms disclosed, but on the contrary, example embodiments are to cover all modifications, equivalents and/or alternatives, functional and/or structural, falling within the scope of the disclosure. Like numbers refer to like or similar elements throughout the description of the Figures.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g. "between" versus "directly between", "adjacent" versus "directly adjacent", etc.).

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will further be understood that the terms "comprises", "comprising", "includes" and/or "including", when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries should be interpreted as having a meaning that is consistent with their meaning in the context of the relevant art and will not be interpreted in an idealized or overly formal sense unless expressly so defined herein.

In the following Figures, three orthogonal spatial directions each may be differentiated (Cartesian coordinate system x, y, z), and these are each indicated at the right margin of the Figures. FIG. 1a shows an embodiment of a fluid sensor 100 from two perspectives. The top illustration shows a sectional view along an axis AB which is also visible in the top view illustrated at the bottom. In the embodiment illustrated in FIG. 1a, the fluid sensor 100 includes a substrate 80 which comprises a recess 70 for receiving a fluid to be examined. In this and in the following embodiments any substrate 80 may be used here. For example, printed circuit boards, glass, porcelain etc. are possible just like semiconductor materials, e.g. silicon (Si), germanium (Ge), gallium arsenide (GaAs), indium antimonide (InSb), zinc selenide (ZnSe) or cadmium sulfide (CdS), etc. in different dopings and embodiments or shapes, e.g. as a disc, or wafer. In some embodiments, the substrate 80 is at least part of a semiconductor wafer.

According to FIG. 1a the fluid sensor 100 is implemented to detect electrical changes in the recess 70 caused by the fluid to be examined. Accordingly, the dimensions of the recess 70 are selected so that the fluid to be examined may enter or pass the recess, respectively, e.g. the recess 70 may correspond to an opening or a trench passing the substrate 80 which corresponds to a diameter of less than 1 cm, 1 mm, 1 µm, etc. As it is explained in more detail below, also a recess 70a having the same dimensions may at least partially be surrounded by a gate of a transistor. The fluid may here and in the following correspond to a substance which is present in a liquid or gaseous form or as a plasma and is for example to be examined, detected or monitored or controlled with respect to chemical changes. This may be done according to FIG. 1a based on chemical changes caused in the recess 70 which cause electrical changes.

Electrical changes herein are changes of electrical characteristics. E.g. the fluid may cause changes of charge, potential changes, potential difference changes, changes of a relative dielectricity, currents, voltages, etc. For example, dipoles may be formed by the fluid or the formation may be changed so that a change of dipole moments may be detected by the fluid sensor as a measure for a spatial charge separation.

FIG. 1a illustrates a further embodiment, wherein optionally (dashed lines) the fluid sensor 100 further includes an exterior electrode 10. The exterior electrode 10 at least partially surrounds the recess 70 and is connected or connectable to a reference potential (e.g. ground potential). The exterior electrode 10 may influence an electrical field in the interior of the recess 70, for example the same may shield the recess 70 from exterior fields or predetermine a defined field, e.g. a homogeneous field. In some embodiments, the exterior electrode 10 may also form kind of a Faraday cage with respect to the recess 70.

The exterior electrode 10 may for example be formed by a correspondingly implemented or shaped conductor, e.g. by a metal or a metal coating on the substrate 80. In some embodiments, the exterior electrode 10 may correspond to a delineated doping area of the substrate, e.g. a p- or n-doping of the substrate 80. This delineated doping area is for example demarcated by a p-n transition from an adjoining substrate area, so that at the demarcated doping area a desired potential may be applied.

Figure 1B:
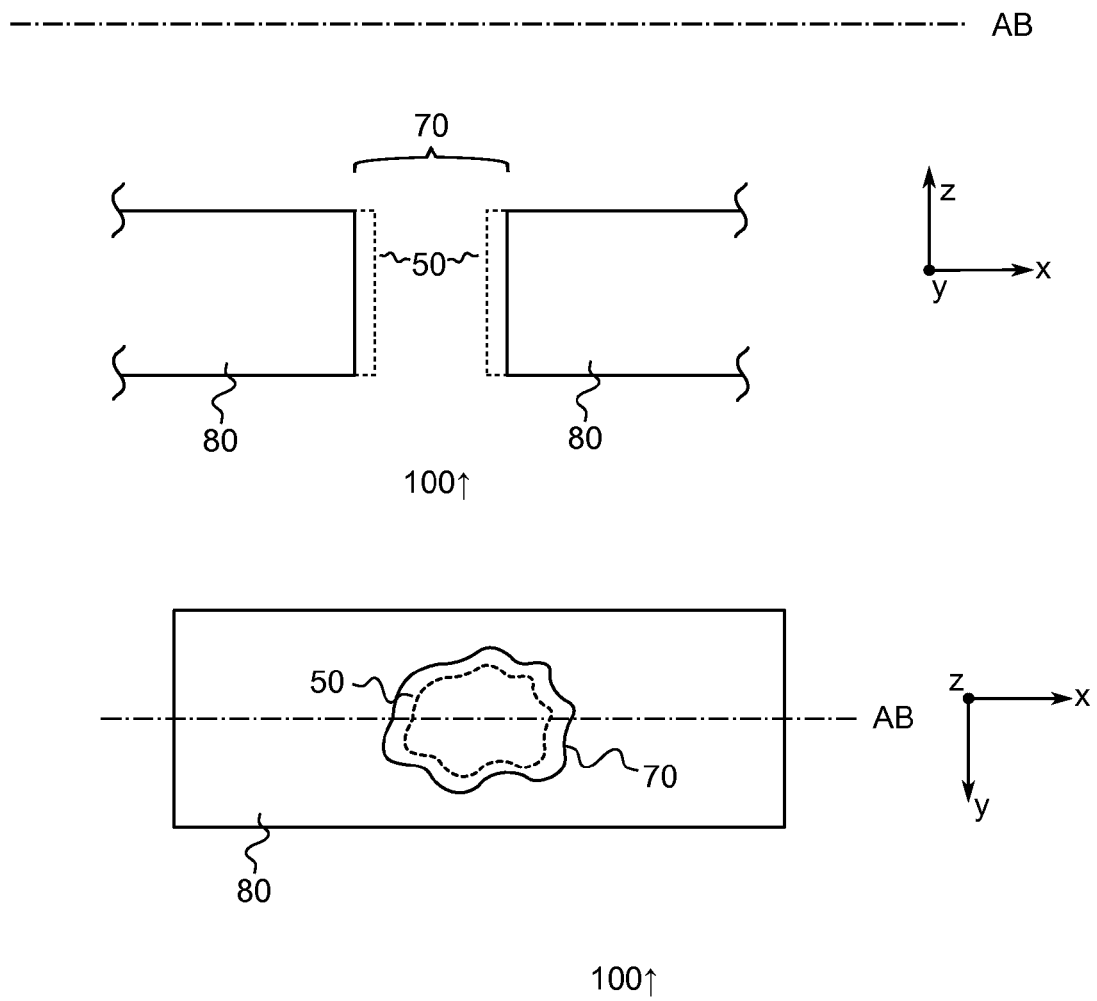
FIG. 1b shows a further embodiment of a fluid sensor from two perspectives with an optional chemically sensitive layer.

FIG. 1b shows a further embodiment of a fluid sensor 100 from two perspectives analog to FIG. 1a. FIG. 1b here shows the fluid sensor as it was already described with reference to FIG. 1a, with the substrate 80 and the recess 70, wherein the fluid sensor 100 in FIG. 1b optionally comprises a chemically sensitive layer 50. The chemically sensitive layer 50 is at least partially arranged in the recess 70. The embodiment shows an arrangement of the chemically sensitive layer 50 around the recess 70. In further embodiments, also a partial or sectional arrangement of the chemical layer 50 within the recess 70 is possible. The chemically sensitive layer 50 is implemented to for example convert chemical reactions, the passage of ions, physical adsorption, chemical adsorption, the change of dipole moments, etc. into electrical changes, for example by changing the charge state or the dielectricity constant.

Figure 1C:
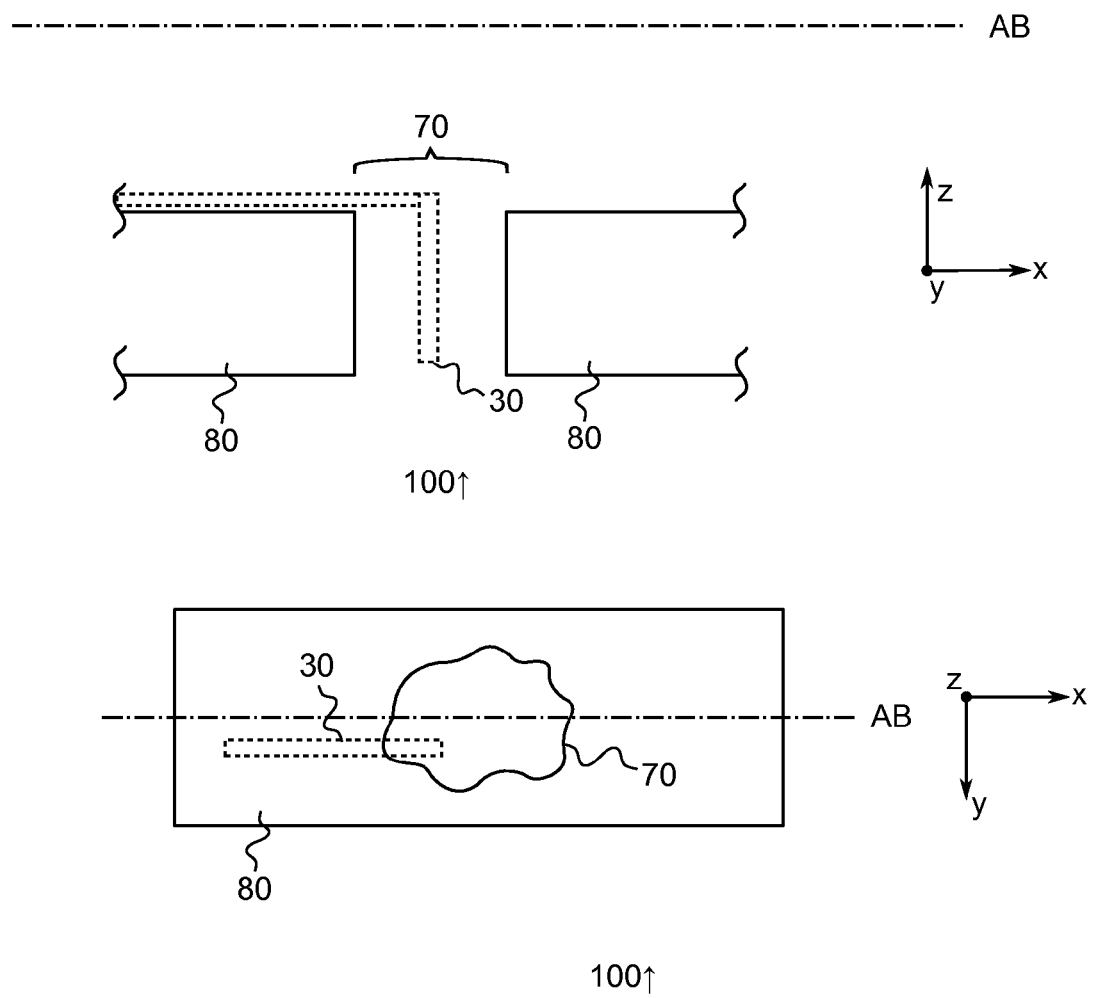
FIG. 1c shows a further embodiment of a fluid sensor from two perspectives with an optional insulated gate of a field effect transistor.

A further embodiment of a fluid sensor 100 is illustrated from two perspectives in FIG. 1c. FIG. 1c here shows the fluid sensor as it has already been described with reference to FIG. 1a, with the substrate 80 and the recess 70. In this embodiment, the fluid sensor 100 optionally includes an insulated gate 30 of a field effect transistor, which is at least partially arranged in the recess 70. Here, for example a contact tab or a contact of the gate 30 may reach into or be at least partially surrounded by the recess 70. The gate 30 then is implemented to detect electrical changes in the recess 70 and make the same measurable or evaluable via the transistor.

Figure 2:
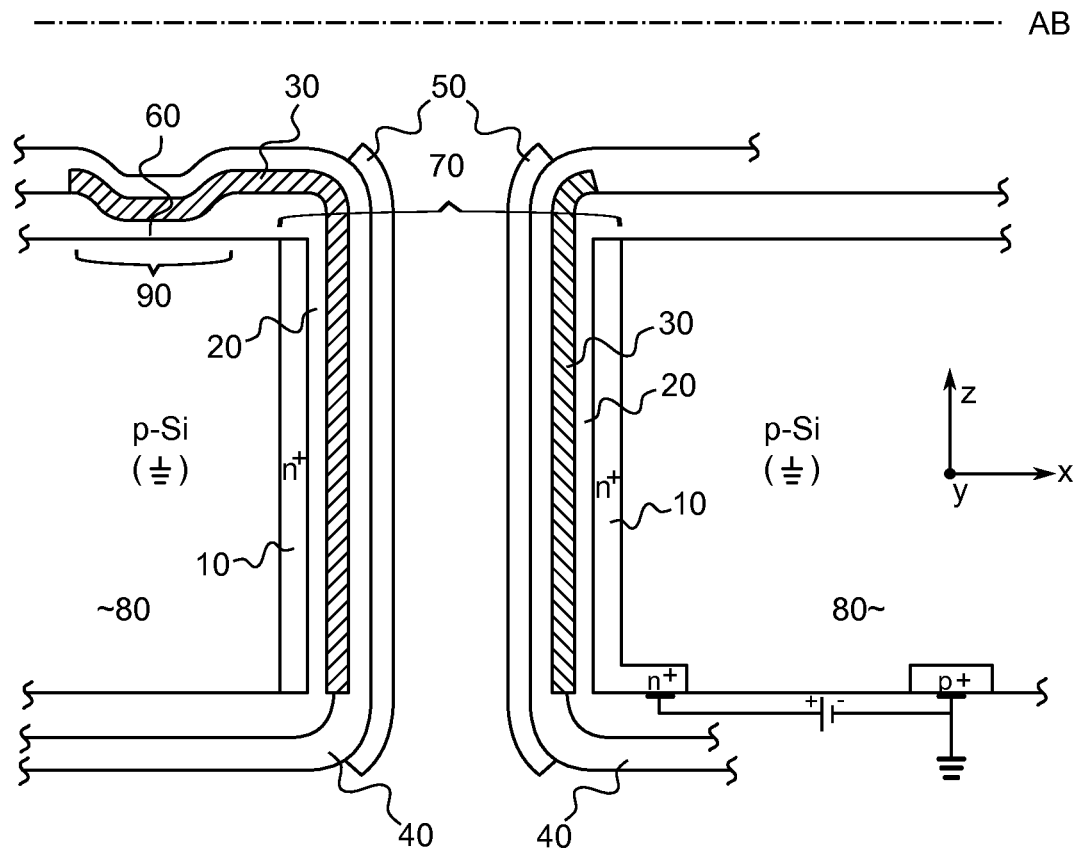
FIG. 2 illustrates an embodiment of a fluid sensor implemented as a hollow cylinder in a cross-sectional view.
Figure 3:
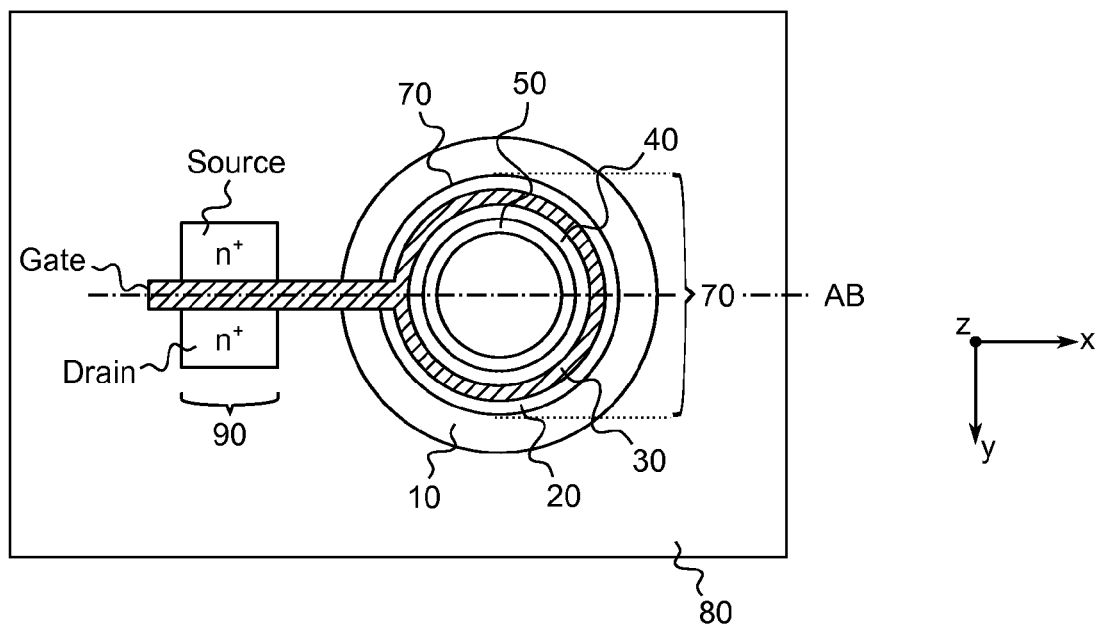
FIG. 3 illustrates an embodiment of a fluid sensor implemented as a hollow cylinder in top view.

FIGS. 2 and 3 illustrate an embodiment of a fluid sensor 100 implemented as a hollow cylinder in a sectional view (FIG. 2) and a top view (FIG. 3), wherein the sectional axis AB is illustrated in both views. In the embodiment illustrated in FIGS. 2 and 3 the substrate is a Si semiconductor substrate which is in this example initially p-doped. In general, also embodiments having dopings complementary to those described here are possible. In other embodiments, the substrate may also be n-doped. FIGS. 2 and 3 show the recess 70 in the center which is here implemented as a via through the substrate 80. In other words, the recess 70 in the illustrated embodiment is implemented as a passage through the substrate 80 from a first side (top in FIG. 2) of the substrate 80 to a second side (bottom in FIG. 2) of the substrate. Further, FIG. 2 shows that the substrate 80 and the exterior electrode 10 in this embodiment are coupled to a reference potential. An electric coupling of the substrate 80 is here executed via a p+-doped area.

In general, via the reference potential in the present embodiment also an operating point of the transistor 90 or consequently also of the fluid sensor 100, respectively, may be set. In other words, the reference potential may be utilized to set a certain sensitivity of the channel with respect to potential changes of the gate on the characteristic curve of the transistor 90. In so far, with a reference potential which corresponds to ground/mass, a self-locking or normally locking FET may be switched off from a power supply so that the same basically receives no power any more. This may for example be advantageous in mobile applications in battery-operated devices with respect to energy efficiency of the device, e.g. mobile radio devices. In other embodiments, also the use of self-conducting or normally conducting FETs is possible. In so far, the embodiments explained with respect to FIGS. 2 to 5 each show a fluid sensor 100 which is implemented to detect an absolute potential change at an electrode 30 caused by a fluid to be examined. The fluid sensor comprises an electrode 30 configured to develop an absolute potential change caused by a fluid to be examined.

In other embodiments, the recess 70 may also be implemented in the form of a trench, in the form of a passage or in the form of a gap which extend from a main surface of the substrate into the substrate or through the substrate. A main surface of a semiconductor substrate 80 is for example a surface of the semiconductor substrate 80 on which further layers may be located, e.g. metal layers, insulation layers, passivation layers, etc. The main surface of such a substrate consequently extends in a lateral direction and is, for example, limited by edges which are given by singulating individual chips or by borders of a wafer. In the embodiments of FIGS. 1a-c in the illustration of FIGS. 1a-c at the top and in FIG. 2 the main surface is at the top, the bottom illustration or FIG. 3, respectively, show top views onto the main surface. The main surface may basically be regarded as plane, e.g. neglecting unevennesses resulting from the semiconductor structure or a manufacturing process (e.g. due to the recess). The main surface may thus also be regarded as a transition area between the substrate 80 or the semiconductor material and possible other layers, like insulation, passivation, metallization.

In the embodiments of FIGS. 1a, 1b, 1c to 3 the recess 70 shows a vertical extent, i.e. perpendicular to the main surface of the substrate 80. It is further assumed that the extent of the recess 70 in the vertical direction is at least twice as large as a lateral extent of the recess 70 along other spatial directions, i.e. in the lateral direction with respect to the main surface.

In the embodiment illustrated in FIGS. 2 and 3, the fluid sensor 100 further includes a transistor 90 which is implemented to detect the electrical changes in the recess 70 e.g. as potential changes. The transistor 90 is implemented as an insulated gate field effect transistor 30, wherein the insulated gate 30 is at least partially arranged within the recess 70. In other embodiments also other transistor types may be used, for example bipolar transistors. The transistor 90 is realized in FIGS. 2 and 3 by two n+-doped areas, separated by a gate insulation layer 60. The actual gate 30 or the gate electrode 30 is partially arranged above the gate insulation layer 60 and thus influences the channel between source and drain (here n+ areas). In so far, in the illustrated embodiment the transistor 90 is arranged outside the recess 70.

In the embodiment illustrated in FIGS. 2 and 3, the fluid sensor 100 further comprises a chemically sensitive layer 50. The chemically sensitive layer 50 is at least partially arranged in the recess 70. The chemically sensitive layer 50 for example is implemented to convert chemical reactions, the passage of ions, physical adsorption, chemical adsorption, etc. into electrical changes, for example a change of the charge state or of the dielectricity constants. These electrical changes then affect the gate 30 and the transistor 90 or its switching or conducting state, so that a chemical change of the fluid to be examined, e.g. ionization or chemical composition leads to the change of an electrical signal which may then be evaluated. Embodiments here are not limited to a certain chemically sensitive material for the chemically sensitive layer 50, for example materials like tin (IV) oxide ($SnO_2$) change their conductivity under the influence of gas. Other materials are zinc oxide, titanium dioxide or organic semiconductor materials like MePTCDI (MePTCDI or DiMePTCDI, respectively, or N,N'-Dimethyl-3,4,9,10-Perylentetracarboxylic diimide). The respective choice of material for the chemically sensitive layer 50 will thus depend on the respective case of application, e.g. which gas or which liquid is to be detected, in what temperature range the sensor is used, the field of use, etc.

In other words, in the interior of the Faraday cage a chemically sensitive layer 50 may be applied wherein due to gases or liquids the formation of charges and/or dipole moments may result and thus a potential in the interior may be changed. The value of the potential change may e.g. be measured by an insulated or "floating" electrode or gate 30 which may be connected to the gate of an MOSFET like with the "floating gate" FET (FGFET).

Possible fields of use are, for example, safety technology like e.g. explosion protection, methane and carbon monoxide detection in mines, hydrogen detection in fuel cells, detection of gas leaks e.g. in natural gas supply or with liquid gas, protection against poisoning, e.g. personal carbon monoxide and hydrogen sulfide monitoring, leakage detection, e.g. in the monitoring of chemical tanks with volatile organic components, solvents or coolants, fire alarm systems e.g. for combustion gas detection of intelligent detectors, drug tests, e.g. breathalyzer tests for road traffic, detection of chemical warfare agents e.g. also for explosives or poisonous gas. Further fields of application are emission measurements, motor control via a Lambda probe, vehicle diagnosis, measurement of gaseous immissions in the inner city traffic, conveniences e.g. air quality in inner city areas, automatic ventilation valve in cars, facility management, extractor hoods, humidity sensors, etc.

As FIGS. 2 and 3 illustrate, the chemically sensitive layer 50 in the recess 70 forms a boundary layer to the fluid to be examined, so that the chemically sensitive layer 50 may offer a direct, relatively large contact to the fluid to be examined. It may further be seen that the chemically sensitive layer 50 surrounds the fluid to be examined in the recess 70 at least partially and at least with respect to two spatial directions. In other words, in FIGS. 2 and 3 three orthogonal spatial directions may be differentiated (Cartesian coordinate system, x, y, z) as it is indicated on the right margin of the Figures. In FIG. 1a, b, c, to 3 it may be detected that the recess 70 which is here formed basically as a hollow cylinder surrounds a passing fluid in the way of a channel. It may further be seen that the recess 70 shows a vertical extent (in z direction, perpendicular to the main surface) which is at least twice as large as a lateral extent of the recess 70 along other spatial directions (x, y directions). In other words it may be seen that the recess extends in the z direction and that the same extends further in the z direction (at least twice as far) than in the x, y directions.

It may further be seen in the embodiment that the insulated gate 30 is arranged at least partially between the chemically sensitive layer 50 and an exterior electrode 10. This arrangement may enable an improved electrical response of the gate 30 to an electrical change of the chemically sensitive layer.

FIGS. 2 and 3 further show that the fluid sensor 100 in this embodiment at least includes an insulation layer 20, 40 which his arranged at least partially between the substrate 80 and the chemically sensitive layer 50. The insulated gate 30 is at least partially separated from the chemically sensitive layer 50 and the exterior electrode 10 by one or several insulation layers 20, 40, in the embodiment of FIGS. 2 and 3 by the two insulation layers 20 and 40. The transistor 90 further includes a gate oxide layer 60 which is thinner than the one or several insulation layers 20, 40. This may contribute to an improved sensitivity of the transistor 90 or the sensor 100, respectively. As an insulation/passivation material for example oxide layers are possible, e.g. silicon dioxide, in other implementations also silicon nitride, hafnium dioxide, polymers, etc.

The setup of the Faraday cage 10, in the embodiment of FIGS. 2 and 3, consists of the exterior electrode 10 to which a potential is applied from the outside, here a reference potential or ground potential. This potential defines the at least virtually constant potential in the interior of the cage 10. The "floating electrode" or the gate 30 is insulated by a first insulator layer 20 and a second insulator layer 40. Onto the insulator layer 40, the chemically sensitive layer 50 is applied which is responsible for the chemical reaction and is not electrically contacted. This layer may be insulating, semiconducting or conducting. The "floating electrode" is connected to the gate 30 of the MOS transistor 90, wherein the proportional extent outside the Faraday cage 10 here is smaller than the proportional extent within the Faraday cage. In general it may be assumed that the proportional extent outside the Faraday cage 10 ought to be small in order to minimize exterior potential influences and/or marginal influences. The gate oxide 60 of the transistor 90 is clearly thinner than the insulation oxides 20 and 40. Each charge transfer, change of the work function etc. of the chemically sensitive layer 50 in the interior of the cage 10 leads a potential change. Thus, also the potential of the "floating electrode" 30 changes which controls the source/drain current of the field effect transistor 90. For conductive liquids, outside the cage 10 a potential or reference contact may be available in order to prevent charging effects.

Apart from that, FIGS. 2 and 3 also show a fluid sensor 100 wherein a chemically sensitive layer 50 is arranged in a passage 70 of a substrate 80 for receiving a fluid to be examined. The sensor 100 further includes a transistor 90 which is implemented to detect an electrical change of the chemically sensitive layer 50 in the passage 70 caused by the fluid to be examined. The passage 70 is in this embodiment implemented basically in the shape of a hollow cylinder, wherein the transistor 90 is implemented as an insulated gate 30 field effect transistor. The insulated gate 30 extends at least partially along a wall of the hollow cylinder-shaped recess 70 of the substrate 80. The fluid sensor 100 further includes an exterior electrode 10 which at least partially surrounds the recess 70.

It may further be seen in the embodiments that the area of the gate 30 in the range of the shielded range, i.e. in the recess 70 and within the exterior electrode 10 is larger than the area outside the shielded range. The ratio of those areas may in embodiments also determine the influence of exterior fields on to the fluid sensor 100. It is to be assumed that within the shielded area electrical changes of the gate 30 are mainly caused by the fluid as exterior influences are basically shielded. Outside the shielded area, for example in FIGS. 2 and 3 in the area left of the recess 70 in which the gate electrode 30 extends towards the source and drain terminals, i.e. to the actual gate of the FET, this may also be influenced by the exterior fields due to non-existent shielding in this embodiment. In so far, in embodiments an area of the insulated gate electrode 30 located within the exterior electrode 10 or the recess 70 may be larger, e.g. at least twice or three times as large as an area of the gate electrode 30 which is located outside the exterior electrode 10 or the recess 70.

Figure 4:
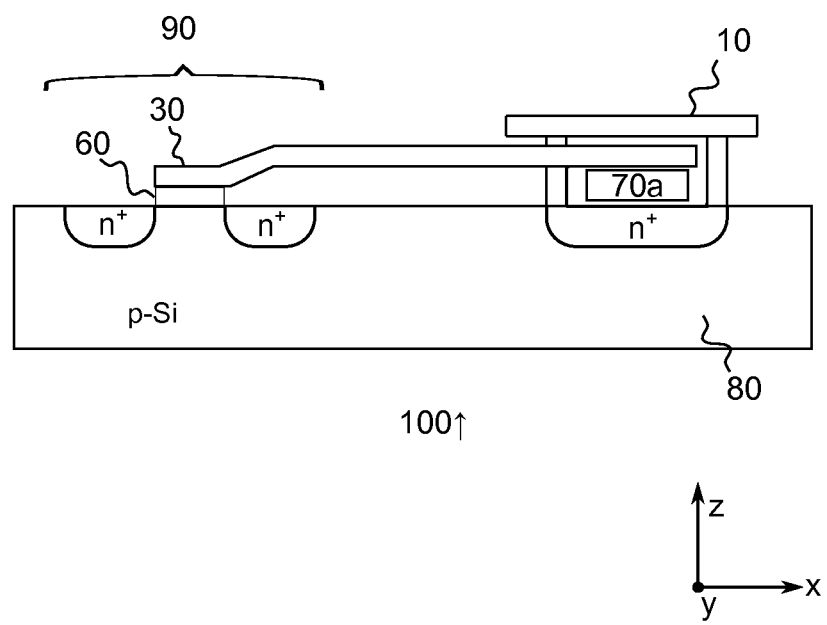
FIG. 4 shows an embodiment of a fluid sensor with a field effect transistor with a recess at least partially surrounded by an insulated gate.

FIGS. 2 and 3 also illustrate a fluid sensor 100 with a transistor 90 and further optional components. FIG. 4 shows an embodiment of a fluid sensor 100 with a transistor 90 with a recess 70a which is at least partially surrounded by an insulated gate 30 in the sectional view (see indicated coordinate system). The fluid sensor is implemented to detect an electrical change e.g. of a chemically sensitive layer 50 caused by a fluid to be examined. The transistor 90 is implemented as an insulated gate 30 field effect transistor and the insulated gate 30 and a recess 70a for receiving the fluid to be examined are at least partially surrounded by a common shielding electrode 10. The recess 70a is here outside a substrate 80 on which the transistor 90 is formed. FIG. 4 here further illustrates the gate oxide layer 60 of the transistor. In the embodiment of FIG. 4 the exterior electrode 10 is for example formed by a p+-doped area in the substrate 80, two vias or contact holes and a superimposed metal layer. These components enclose the recess 70a at least partially. The gate 30 protrudes into the recess 70a and is at least partially shielded by the exterior electrode 10. In this embodiment, the recess 70a is formed with respect to the gate 30 and together with the gate 30 lies outside the substrate 80.

Figure 5:
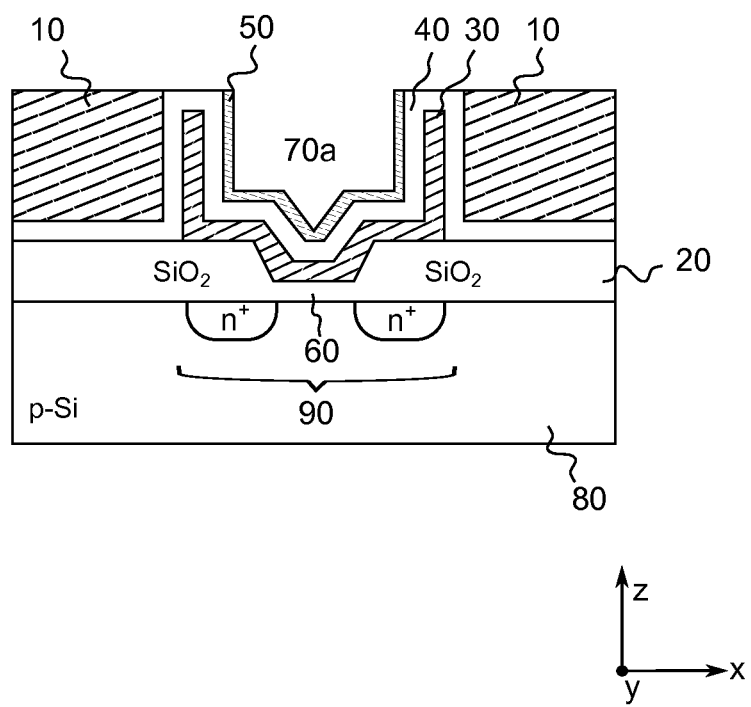
FIG. 5 shows a further embodiment of a fluid sensor with a field effect transistor with a recess at least partially surrounded by an insulated gate.

FIG. 5 shows a further embodiment of a fluid sensor 100 having a field effect transistor 90 with a recess 70a which is at least partially surrounded by an insulated gate 30 in a sectional view (see indicated coordinate system). In the embodiment illustrated in FIG. 5, the transistor 90 is formed on the substrate 80 by means of the already above-described n+-doped areas for source and drain and by means of the gate oxide layer 60 which his implemented thinner opposite to the insulation layer 20 located on the substrate 80. FIG. 5 further shows the gate 30 which is here formed pot-shaped above the substrate 80 and extends from an area above the gate oxide layer 60 away from the substrate 80.

The pot-shaped gate 30 is further surrounded by a second insulation layer 40 and at least in this embodiment lies between the two insulation layers 20 and 40. As illustrated in FIG. 5, the pot-shaped gate 30 is further laterally at least partially surrounded by the exterior electrode 10. Via a potential applied to the exterior electrode 10 the potential in the pot-shaped gate 30 may be predetermined, i.e. be kept constant or the interior 70a of the gate 30 may basically be kept field-free. As the innermost layer, FIG. 5 further shows a chemically sensitive layer 50 which fulfills the already above-mentioned functions. In so far, FIG. 5 illustrates a further embodiment wherein the recess 70a is formed with respect to the gate 30 and lies outside the substrate 80.

Figure 6:
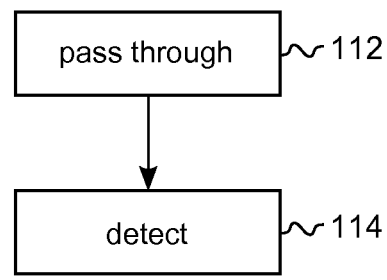
FIG. 6 shows a block diagram of an embodiment of a method for examining a fluid.

FIG. 6 shows a block diagram of an embodiment of a method for examining a fluid. The method for examining the fluid includes passing the fluid 112 through a recess 70 of a substrate 80. The method further includes detecting 115 an electrical change in the recess 70. Such a method may also be executed automatically, for example with the help of a computer program which gives corresponding control commands to valves or to other components in order to detect and evaluate the electrical changes in the recess 70 as potential changes, e.g. with the help of the transistor 90.

Features disclosed in the above description, the following claims and the accompanying drawings may both individually and also in any combination be of importance and implemented for the implementation of an embodiment in its different forms.

Although some aspects were described in the context of a device, it is obvious that those aspects also represent a description of a corresponding method, so that a block or a member of a device is also to be regarded as a corresponding method step or as a feature of a method step. Analog to that, aspects described in context with or as a method step also represent a description of a corresponding block or detail or feature of a corresponding device.

The above embodiments merely represent an illustration of the principles of the present invention. It is obvious that modifications and variations of the arrangements and details described herein are obvious to other persons skilled in the art. It is thus obvious that the invention is merely limited by the scope of the following patent claims and not by the specific details presented herein by the description and the explanation of the embodiments.

What is claimed is:

1. A fluid sensor comprising a substrate including a recess for receiving a fluid to be examined, the fluid sensor further comprising an exterior electrode, wherein the exterior electrode at least partially surrounds the recess and is connected or connectable to a reference potential, and a transistor implemented to detect electrical changes in the recess caused by the fluid to be examined as electrical potential changes in the recess, wherein the transistor is an insulated gate field effect transistor, wherein an insulated gate of the insulated gate field effect transistor is arranged at least partially in the recess,
wherein the fluid sensor further comprises a chemically sensitive layer at least partially arranged in the recess,
wherein the insulated gate is at least partially arranged between the chemically sensitive layer and the exterior electrode,
wherein the insulated gate is at least partially separated from the chemically sensitive layer and the exterior electrode by at least one insulation layer.

2. The fluid sensor according to claim 1, wherein the exterior electrode corresponds to a demarcated doped area of the substrate.

3. The fluid sensor according to claim 1, wherein at least a portion of the transistor is arranged outside the recess.

4. The fluid sensor according to claim 1, wherein the chemically sensitive layer in the recess forms a boundary layer to the fluid to be examined.

5. The fluid sensor according to claim 1, wherein the chemically sensitive layer surrounds the fluid to be examined in the recess at least partially and at least with respect to two spatial directions.

6. The fluid sensor according to claim 1, further comprising at least one insulation layer at least partially arranged between the substrate and the chemically sensitive layer.

7. The fluid sensor according to claim 1, wherein a gate oxide layer of the transistor is thinner than the at least one insulation layer.

8. The fluid sensor according to claim 1, wherein the recess comprises a vertical extent which is at least twice as large as a lateral extent of the recess along other spatial directions.

9. The fluid sensor according to claim 1, wherein the recess is implemented in the form of a trench, in the form of a passage or in the form of a gap.

10. The fluid sensor according to claim 1, wherein the recess is implemented as a passage through the substrate from a first side of the substrate to a second side of the substrate.

11. The fluid sensor according to claim 1, wherein the recess corresponds to a passage which is generally shaped as a hollow cylinder, wherein the insulated gate of the insulated gate field effect transistor at least partially extends along a wall of the hollow-cylinder-shaped passage of the substrate, and wherein the exterior electrode at least partially surrounds the passage.

12. The fluid sensor according to claim 1, wherein the substrate is at least a part of a semiconductor wafer.

13. A fluid sensor comprising a recess for receiving a fluid to be examined, and a transistor which is implemented to detect an electrical change caused by the fluid to be examined, wherein the transistor is an insulated gate field effect transistor and an insulated gate of the insulated gate field effect transistor and the recess are at least partially surrounded by a common shielding electrode,
wherein the insulated gate of the insulated gate field effect transistor is arranged at least partially in the recess,
wherein the fluid sensor further comprises a chemically sensitive layer at least partially arranged in the recess,
wherein the insulated gate is at least partially arranged between the chemically sensitive layer and the common shielding electrode,
wherein the insulated gate is at least partially separated from the chemically sensitive layer and the common shielding electrode by at least one insulation layer.

14. The fluid sensor according to claim 13, wherein the recess lies outside a substrate on which the transistor is formed.

15. A method for examining a fluid, comprising:
passing the fluid through a recess of a substrate, wherein the recess is at least partially surrounded by an exterior electrode;
detecting an electrical change in the recess using a chemically sensitive layer at least partially arranged in the recess and a transistor which is configured to detect the electrical change as a change of an electrical potential in the recess, wherein the transistor is an insulated gate field effect transistor, wherein an insulated gate of the insulated gate field effect transistor is arranged at least partially in the recess, wherein the insulated gate is at least partially arranged between the chemically sensitive layer and the exterior electrode, wherein the insulated gate is at least partially separated from the chemically sensitive layer and the exterior electrode by at least one insulation layer; and
at least partially shielding the transistor in the recess using a reference potential.

* * * * *